US009855000B2

(12) United States Patent
Lansdorp et al.

(10) Patent No.: US 9,855,000 B2
(45) Date of Patent: Jan. 2, 2018

(54) TRANSDERMAL ANALYTE SENSING DEVICE

(71) Applicant: Milo Sensors, Inc., Santa Barbara, CA (US)

(72) Inventors: Bob Lansdorp, Vancouver (CA); Evan Strenk, Santa Barbara, CA (US); Netz Arroyo, Santa Barbara, CA (US); Daniel Imberman, Santa Barbara, CA (US)

(73) Assignee: Milo Sensors, Inc., Santa Barbara, CA (US)

( * ) Notice: Subject to any disclaimer, the term of this patent is extended or adjusted under 35 U.S.C. 154(b) by 0 days.

(21) Appl. No.: 15/158,258

(22) Filed: May 18, 2016

(65) Prior Publication Data

US 2016/0338627 A1    Nov. 24, 2016

Related U.S. Application Data

(60) Provisional application No. 62/163,284, filed on May 18, 2015.

(51) Int. Cl.
| | |
|---|---|
| *A61B 5/05* | (2006.01) |
| *A61B 5/1486* | (2006.01) |
| *A61B 5/00* | (2006.01) |
| *A61B 5/145* | (2006.01) |

(52) U.S. Cl.
CPC ........ *A61B 5/1486* (2013.01); *A61B 5/14546* (2013.01); *A61B 5/681* (2013.01); *A61B 5/14532* (2013.01)

(58) Field of Classification Search
CPC combination set(s) only.
See application file for complete search history.

(56) References Cited

U.S. PATENT DOCUMENTS

| | | |
|---|---|---|
| 5,944,661 A | 8/1999 | Swette et al. |
| 6,394,994 B1 | 5/2002 | Vilambi et al. |
| 2004/0140209 A1 | 7/2004 | Choi et al. |
| 2005/0010093 A1 | 1/2005 | Ford et al. |
| 2010/0000882 A1 | 1/2010 | Wang et al. |
| 2011/0009727 A1 | 1/2011 | Mensinger et al. |

(Continued)

OTHER PUBLICATIONS

World Intellectual Property Organization, International Search Report and Written Opinion for International Application No. PCT/2016/033105, dated Aug. 19, 2016, 10 total pages.

*Primary Examiner* — Navin Natnithithadha
*Assistant Examiner* — Eric Messersmith
(74) *Attorney, Agent, or Firm* — SoCal IP Law Group LLP; Mark A. Goldstein; Nikki M. Dossman

(57) ABSTRACT

There is disclosed a transdermal analyte sensor device. The device includes a sensor cartridge having a membrane permeable to a target analyte transdermally received from a subject, a reservoir containing a fluid to receive the target analyte through the membrane and an enzyme to react with the target analyte to form a byproduct, a working electrode to generate an electrical current based on a concentration of a byproduct, and a cartridge electrical contact to transmit the electrical current. The device also includes a device body having a device electrical contact to receive the electrical current from the cartridge electrical contact, a transmitter to transmit a signal based on the electrical current to a monitoring device, and a cartridge receptacle to receive the sensor cartridge and position the membrane to contact skin of the subject.

26 Claims, 15 Drawing Sheets

(56) References Cited

U.S. PATENT DOCUMENTS

| | | |
|---|---|---|
| 2012/0252046 A1 | 10/2012 | Fei et al. |
| 2013/0334042 A1 | 12/2013 | Grieve et al. |
| 2014/0242710 A1 | 8/2014 | Suri et al. |
| 2017/0086714 A1 | 3/2017 | Nothacker et al. |

TRANSDERMAL ANALYTE SENSING DEVICE

RELATED APPLICATION INFORMATION

This patent claims priority from provisional application No. 62/163,284 filed on May 18, 2015, entitled "TRANSDERMAL ALCOHOL SENSING DEVICE" which is incorporated by reference in its entirety.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

Field

This disclosure relates to transdermal analyte sensing. The device described herein allows a user to monitor transdermal analyte concentration and estimate blood analyte concentration.

Description of the Related Art

An alcoholic beverage consumer can have difficulty estimating a level of intoxication, or blood alcohol concentration. This is in part because various factors influence intoxication levels. These factors include the varying alcoholic content of alcoholic beverages and the consumer's hydration level, metabolism, and recent food consumption. Further, a consumer's ability to estimate intoxication level based on how intoxicated the consumer feels decreases with increasing alcohol consumption. Because the consumer cannot reliably estimate intoxication level, the consumer may not know if the consumer's blood alcohol concentration exceeds a legal limit, e.g., for driving or boating. Accurate information about blood concentrations of alcohol and other analytes, such as glucose and urea, can be useful.

DETAILED DESCRIPTION

A system and method for sensing blood analytes and their concentration in subjects is described herein. The system enables determination of a subject's blood analyte concentration via a wearable sensor and viewing the determination via an app on the subject's mobile device. Throughout this description, the embodiments and examples shown should be considered as exemplars, rather than limitations on the apparatus and methods described.

Sensing devices described herein estimate a blood analyte concentration of a subject through the subject's skin. The blood analyte can be alcohol, glucose, urea, or other analytes present in blood. The device includes a device body and a sensor cartridge. The analyte diffuses through the skin and into the sensor cartridge via a membrane, and an electrical current is generated based on a concentration of the analyte. The sensor cartridge can be removably coupled to the device body in such a way that electrical contact can be made. The device body receives the electrical current from the sensor cartridge and transmits a signal based on the current to a receiver, such as a mobile device. An estimated blood analyte concentration is determined based on the electrical signal. Further, additional information input in the receiver, such as subject weight, gender, and alcoholic beverage consumption may be used to assist in the blood analyte concentration estimation.

Figure 1:
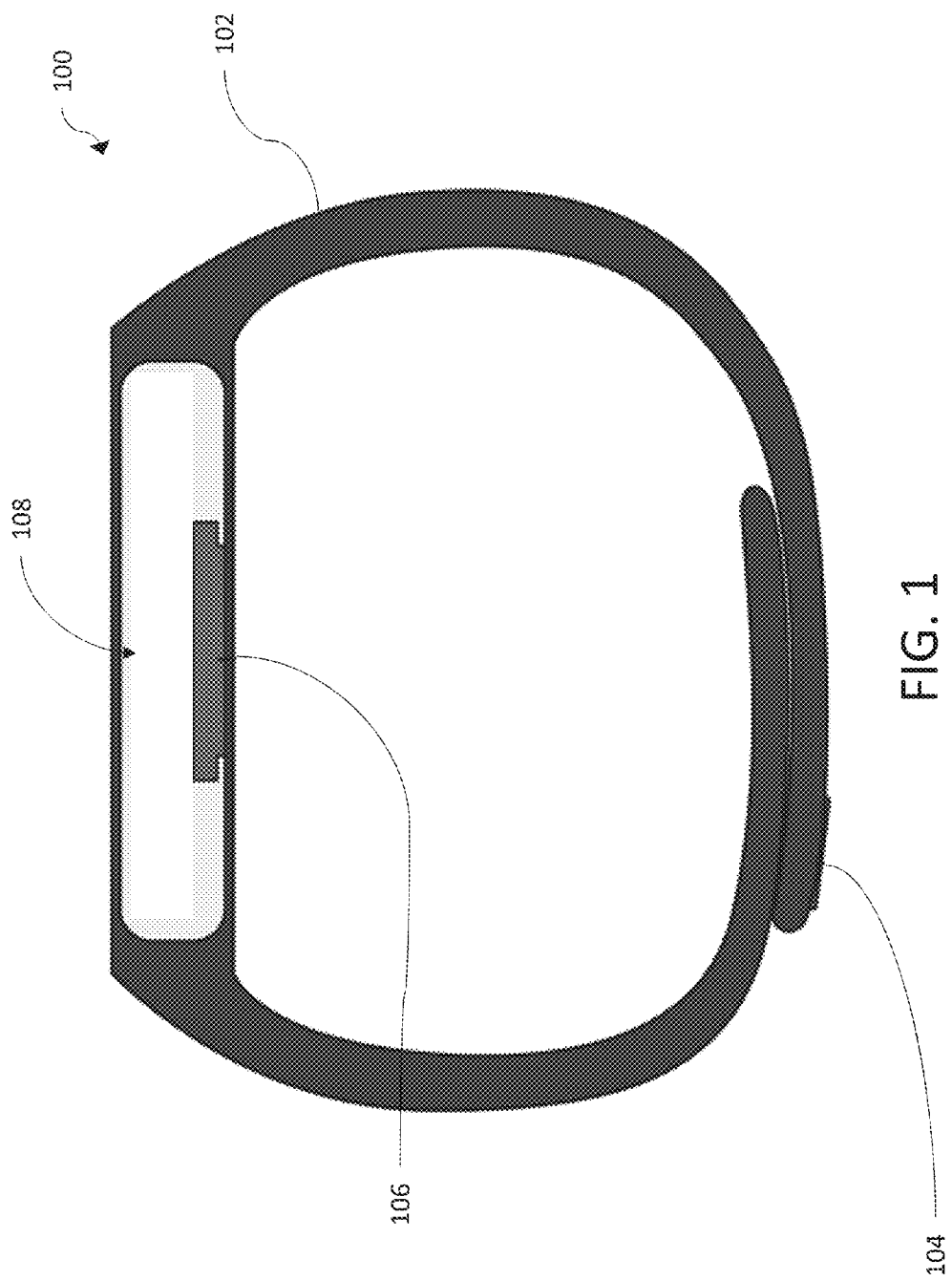
FIG. 1 is a block diagram of a sensor device.

FIG. 1 shows a block diagram (side view) of a sensor device 100 that can be worn by a subject. This sensor device 100 can include a wristband 102 that can be fastened around a subject's wrist via a fastener 104. The fastener 104 can be a snap, a hook-and-loop fastener, a buckle, a magnetic fastener, or any other suitable fastener. The wristband may be made from any of a variety of materials, including, without limitation, silicone rubber, polyethylene, cotton, or polyester. Although shown and described herein as a wristband or bracelet, the device body may be included in any device, article or item that maintains regular contact with human skin, including anklets and necklaces. In addition, the sensor cartridge may also be included in hat brims and eyeglass arms. In all of these configurations the sensor cartridge and other functionality described herein may be included and implemented. The sensor device 100 includes a sensor cartridge 106 positioned adjacent the subject's skin and includes a device body 108 that removably receives the sensor cartridge 106.

Figure 2:
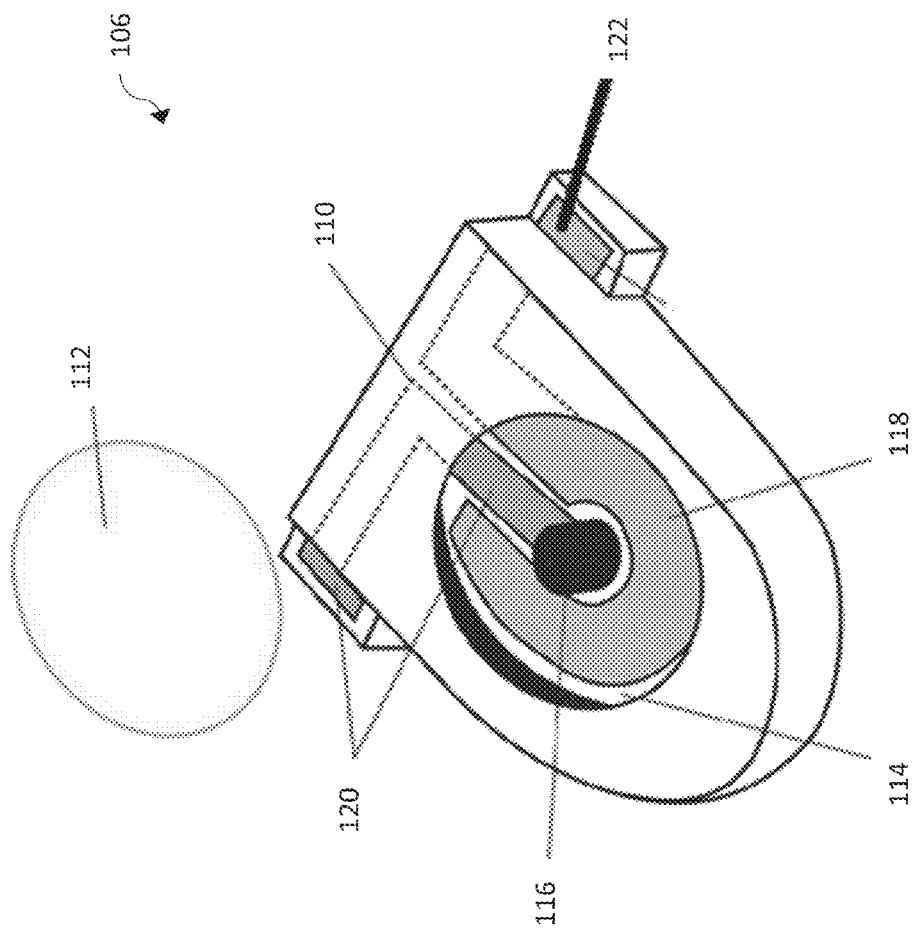
FIG. 2 is a partially exploded block diagram of a sensor cartridge for a sensor device.
Figure 3:
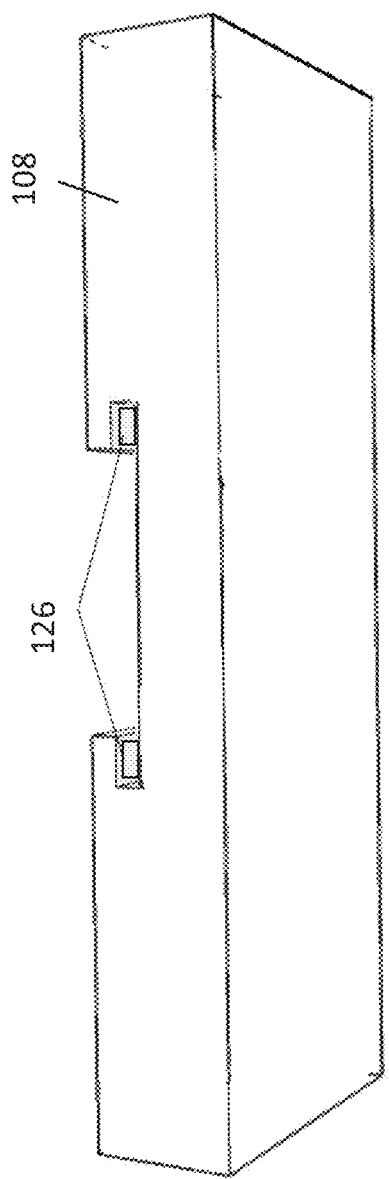
FIG. 3 is a block diagram of a device body of a sensor device.
Figure 4A:
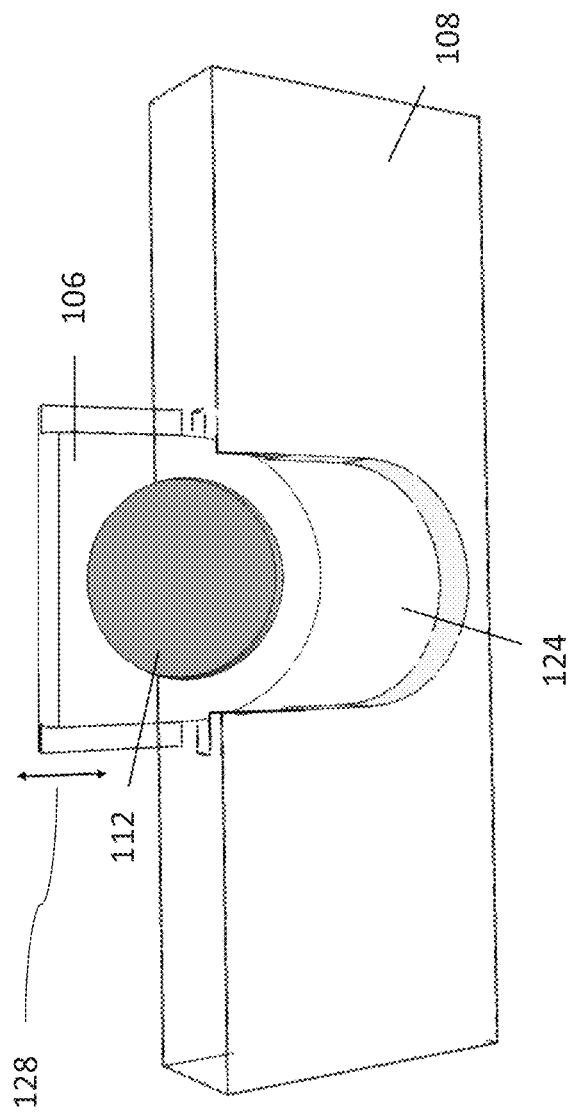
FIG. 4A is a block diagram showing insertion of a sensor cartridge into a device body.

Referring now to FIG. 2, the sensor cartridge 106 includes an analyte-permeable microporous membrane 112. As shown in FIGS. 3 and 4A, device body 108 has a receptacle 124 that slidably receives sensor cartridge 106, as shown by arrow 128. When the sensor cartridge is positioned in receptacle 124 and the subject wears the sensor device 100, the membrane 112 is positioned in contact with the skin of the subject. The sensor cartridge 106 can be removed from the receptacle 124 once its lifespan has expired (e.g., about 12 to 24 hours), and it can be replaced with a fresh sensor cartridge.

Figure 4B:
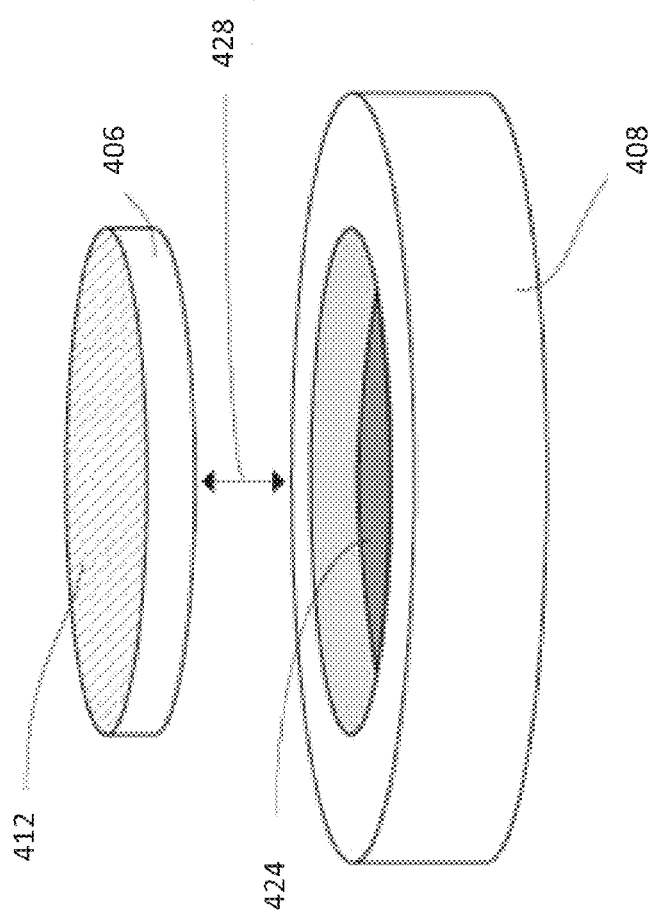
FIG. 4B is a block diagram showing insertion of another sensor cartridge into a another device body.

FIG. 4B shows insertion of a different sensor cartridge configuration into a different device body configuration. Device body 408 has a receptacle 424 that receives sensor cartridge 406, as shown by arrow 428, and retains the sensor cartridge 406 via a friction fit. When the sensor cartridge is positioned in receptacle 424 and the subject wears the sensor device, membrane 412 is positioned in contact with the skin of the subject.

Figure 5:
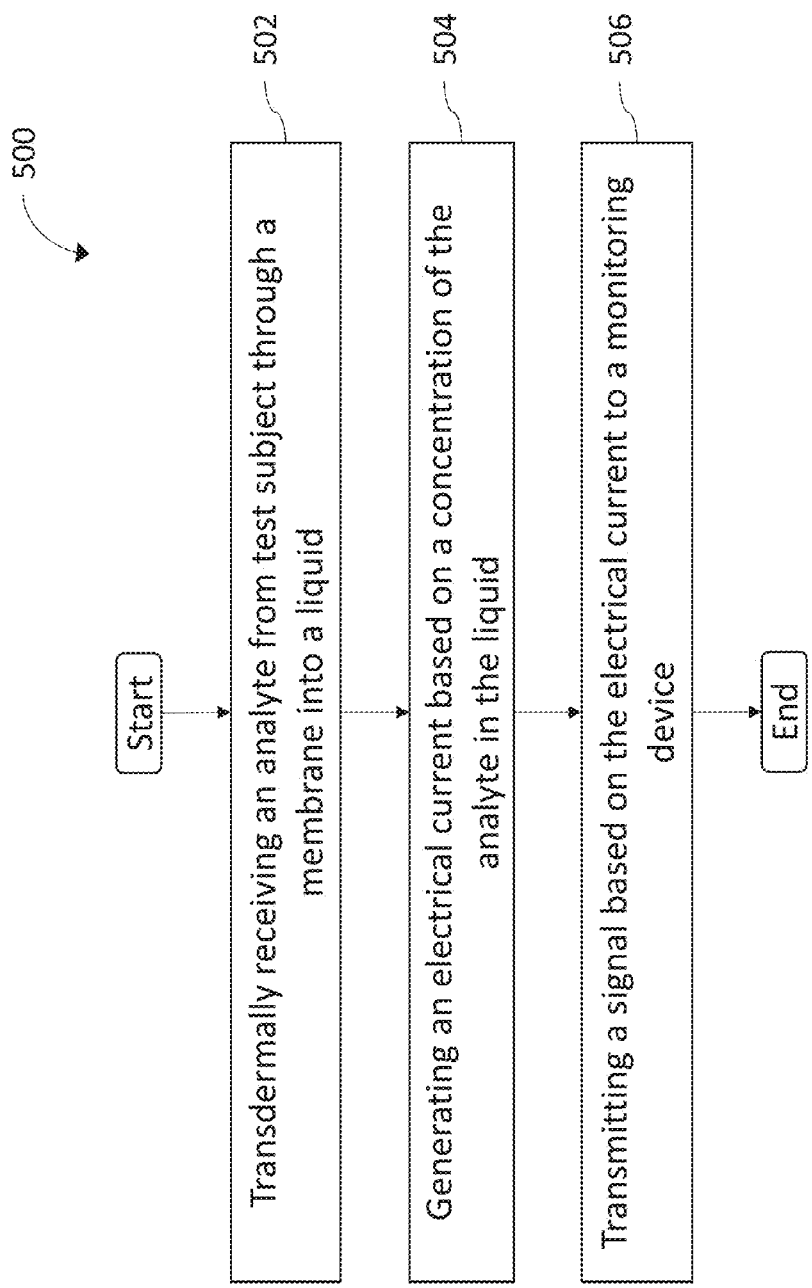
FIG. 5 is a flow chart of a method of transdermal analyte sensing.

As shown in FIG. 5, the sensor device 102 can be used for a transdermal analyte sensing method 500. At step 502, an analyte is transdermally received from a subject's skin through the membrane 112. For example, the membrane 112 can be permeable to ethanol, glucose or urea. For sensing of ethanol, the membrane 112 can be composed of polyethylene, have a thickness of around 25 micrometers and a diameter of about 10 mm, which is sufficient to enable a detectable flux of ethanol through the contact area with skin. Other membrane materials with similar permeabilities to analytes of interest may include poly-vinyl-chloride (PVC), Polypropylene, Polyimide, Polyamide 6 (Nylon), Polyacrylonitrile, Polystyrene, Polycarbonate, Cellulose acetate, and other polymers.

The membrane may also be composed of two layers: a first layer of low permeability to the analyte of interest, and a second layer of high permeability to the analyte of interest, where the first layer contains holes such that the second layer is partially exposed, resulting in a net permeability that is a fraction of the second layer permeability.

In one example, the membrane permeability is no greater than the permeability of human stratum corneum (the least permeable outer layer of human skin), so that the resulting flux of analyte is limited mainly by the membrane diffusion, and not the human skin. In this way, the device maintains relatively reliable operation, independent of sweatiness, user skin type, etc. The permeability of stratum corneum to ethanol is approximately $3.3*10^{-7}$ cm/s, and thus the membrane permeability would be less than or equal to $3.3*10^{-7}$ cm/s. In another example, the membrane permeability is a factor of five less than the stratum corneum, $6.6*10^{-8}$ CM/S.

The sensor cartridge 106 has a liquid reservoir 114, and the membrane 112 is fastened, for example, using a press-fit fluidic seal, to the sensor cartridge 106 such that the membrane 112 covers the reservoir 114 and a fluid seal maintains a fluid, such as 100 mM phosphate-buffered saline (PBS) or other suitable buffered solutions at suitable ionic strength, in the reservoir 114.

Figure 12:
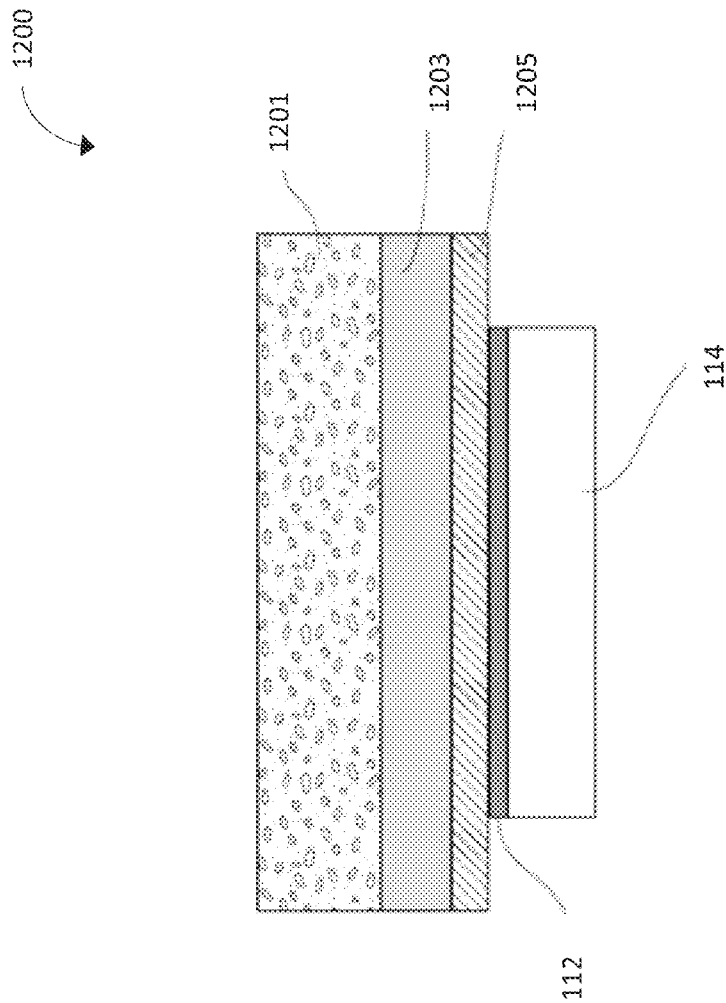
FIG. 12 is a block diagram of layers traversed by an analyte from bloodstream to sensor device.

FIG. 12 shows layers encountered by an analyte traveling from a human bloodstream to a sensor device. The analyte travels from bloodstream 1201 through dermis 1203 into the stratum corneum 1205. From the stratum corneum 1205, the analyte diffuses through membrane 112 into reservoir 114.

At step 504 of FIG. 5, an electrical signal is generated based on a concentration of analyte in the fluid. Specifically, an enzyme-modified working electrode 116 in reservoir 114, as shown in FIG. 2, catalyzes chemical decomposition of the analyte to generate an electrical current. In one example, the enzyme-modified working electrode 116 includes a mixture of enzymes that are pressed into an electrically conductive pellet.

In one example, the sensor device senses ethanol in a subject. To sense ethanol, the enzyme-modified working electrode 116 catalyzes the chemical decomposition of ethanol to convert ethanol that has passed from the subject through the membrane and into the liquid reservoir into an electrical current. The enzyme-modified working electrode 116 may include one or a combination of sensing enzymes such as, for example, alcohol oxidase (AOD), glucose oxidase and/or lactate dehydrogenase, a signal transducing enzyme such as, for example, horseradish peroxidase (HRP), a redox couple such as, for example, ferrocene, forrocyanide, ferricyanide, Prussian blue or any other redox couple, and a matrix made of a combination of a carbon source and an inert binder, for example, a combination of 29% (by weight) graphite and 70% poly tetra fluoro-ethylene (PTFE).

Figure 6A:
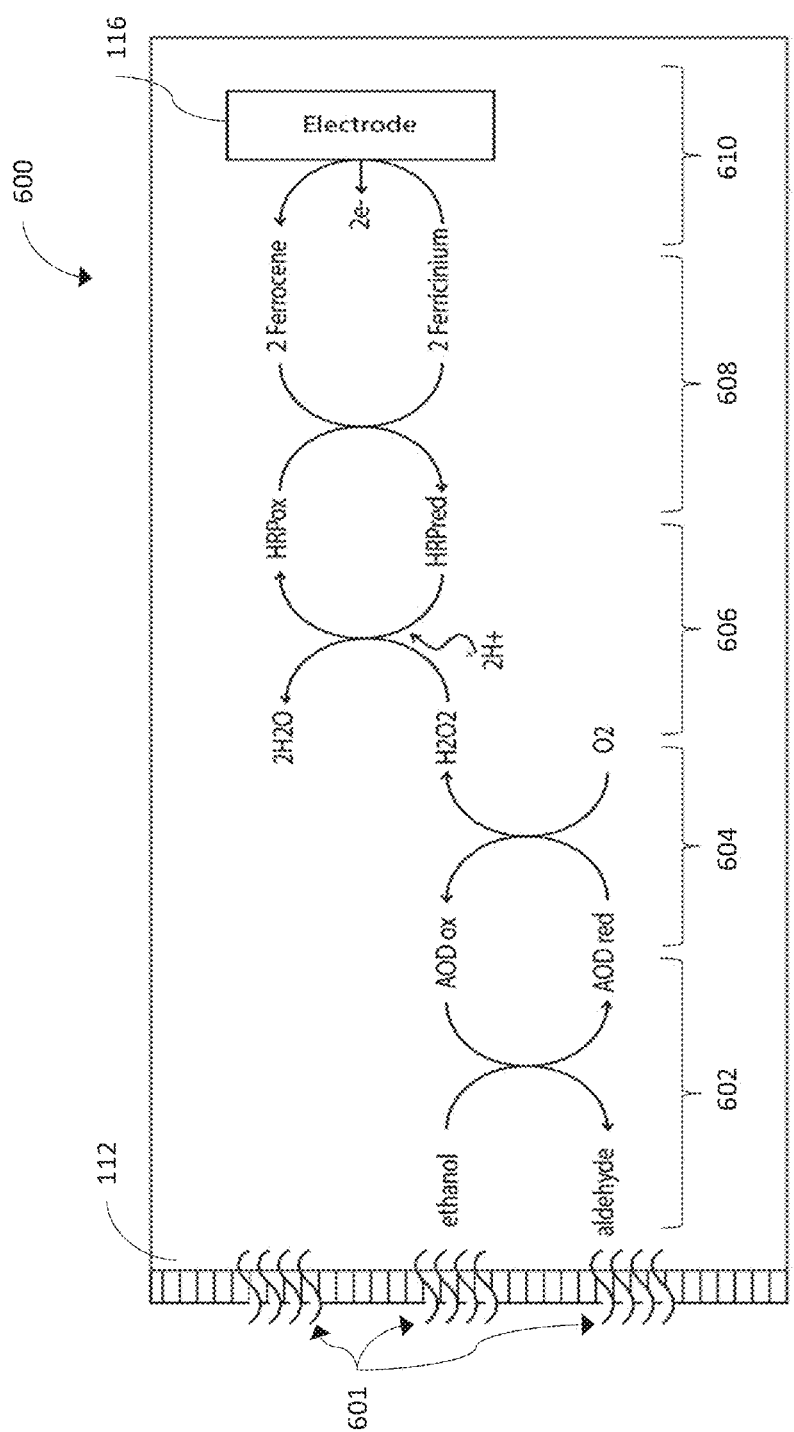
FIG. 6A is a diagram of chemical steps of a method of transdermal analyte sensing.

FIG. 6A shows chemical steps 600 for generating an electrical current based on concentration of analyte in the fluid. At steps 602 and 604, the AOD catalyzes the conversion of ethanol 601 into aldehyde and peroxide. At step 606, the peroxide is converted by HRP into water, and, at step 608, ferrocene is simultaneously oxidized into ferrocinium. As a result, in step 610, an electric potential is created between the enzyme working electrode 116 and a reservoir electrode 118 located in the reservoir 114, shown in FIG. 2, and an electrical current is induced.

Figure 6B:
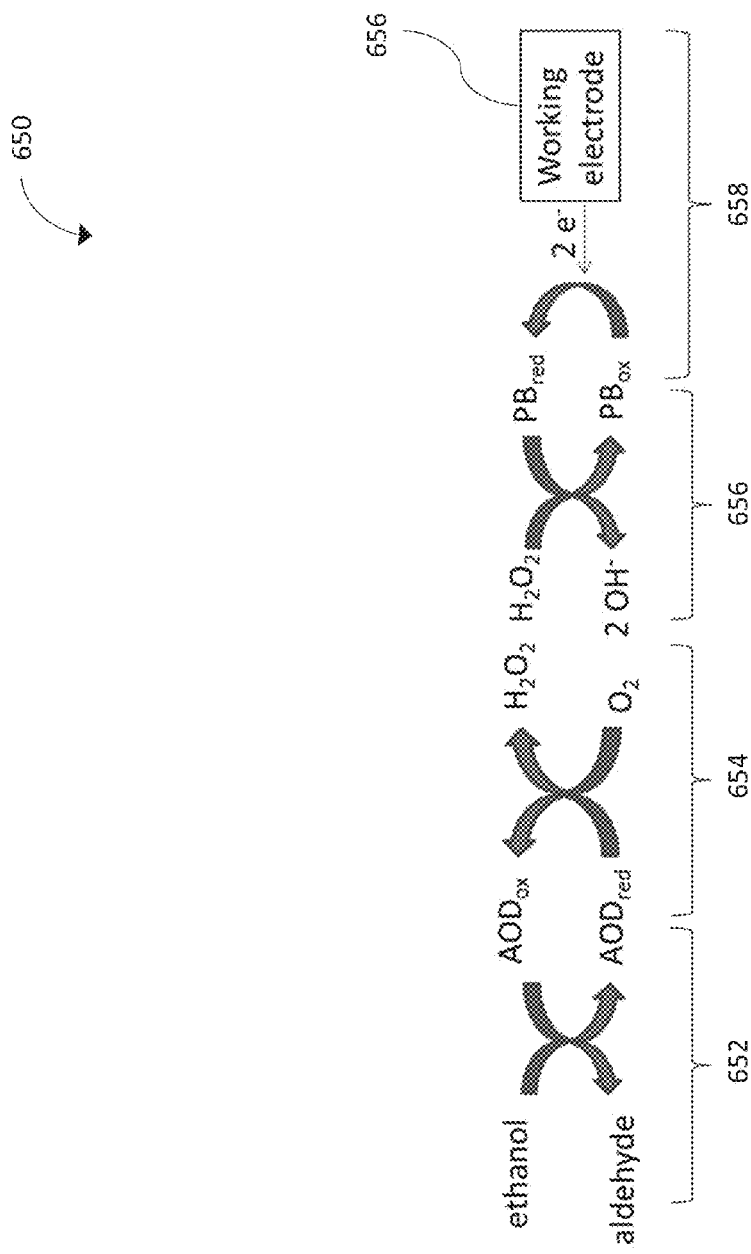
FIG. 6B is a diagram of chemical steps of another method of transdermal analyte sensing.

FIG. 6B is a diagram of chemical steps of another method of transdermal analyte sensing, where the working electrode may be composed of glassy carbon with a thin layer of electrodeposited "Prussian Blue" (ferric ferrocyanide). This Prussian Blue working electrode is sensitive to the presence of hydrogen peroxide in solution. To make a measurement of ethanol, alcohol oxidase in a sensor cartridge forms a byproduct by converting ethanol into hydrogen peroxide that is then detected by the Prussian Blue working electrode. At step 652 of FIG. 6B, ethanol is converted to aldehyde by Alcohol Oxidase (AOD), and, as a result, at step 654, oxygen is consumed to form Hydrogen Peroxide ($H_2O_2$). At step 656, the $H_2O_2$ is converted into two hydroxyl ions ($OH^-$) by the Prussian Blue layer on the working electrode, and at step 658, this results in the flow of 2 electrons. In addition to glassy carbon, the working electrode can be composed of graphite, graphene, or any other electrochemically unreactive materials.

In an example for ethanol sensing, after the subject consumes an alcoholic beverage, ethanol from the alcoholic beverage travels through the subject's digestive system into the blood stream and diffuses through the skin and onto the sensor cartridge 106. There is a delay between peak blood alcohol concentration and peak skin concentration of between one minute and four hours, depending on whether the user is sweaty and other physiological factors. Liquid ethanol passes through the membrane 112 and into the sensor cartridge 106, where it mixes with the PBS and reacts with the enzyme to create hydrogen peroxide. The hydrogen peroxide reacts with either a Prussian Blue working electrode, horseradish peroxidase and mediator, or other peroxide sensor, to create an electrical current.

The electrical current is transmitted from the sensor cartridge 106 into the device body 108 via working electrode contact 120, electrically coupled to the enzyme working electrode 116, and a reference and counter electrode contact 122, electrically coupled to the reservoir electrode 118. In an example, the reservoir electrode 118 and the reference and counter electrode contact 122 are made of Silver (Ag) metal with a coating of silver chloride (AgCl). The AgCl is in equilibrium with NaCl in PBS, which creates a stable reference potential during the detection of ethanol.

In a three-electrode system, the AgCl reference potential is coupled to a transimpedance amplifier to hold the potential of the counter-electrode at a pre-defined value with respect to the reference electrode. The reference and counter electrodes can be combined into one when small electrical current densities, not sufficient to significantly change the reference potential, are being measured. In the case where sufficiently small electrical currents are being measured, a two-electrode system is used, and the potential can more simply be controlled between the working electrode and the combined counter-reference electrode. The sensor device described herein measures relatively small electrical currents (<10 μA), and thus as long as the surface area of the counter-reference electrode is sufficiently high, a two electrode-setup is sufficient to record electrical currents.

As shown in FIGS. 3 and 4, electrical contacts 126 on the device body 108 electrically couple with the working electrode contact 120 and the reference and counter electrode contact 122 on the sensor cartridge 106 when the sensor cartridge 106 is in receptacle 124 on the device body 108. The device body 108 includes electronic components to convert the current from the sensor cartridge 106 into a signal for transmission, such as a BLUETOOTH or other radio signal. The current is in the range from and negative 10 milliamps to positive 10 milliamps and all values inbetween values in between.

Figure 7:
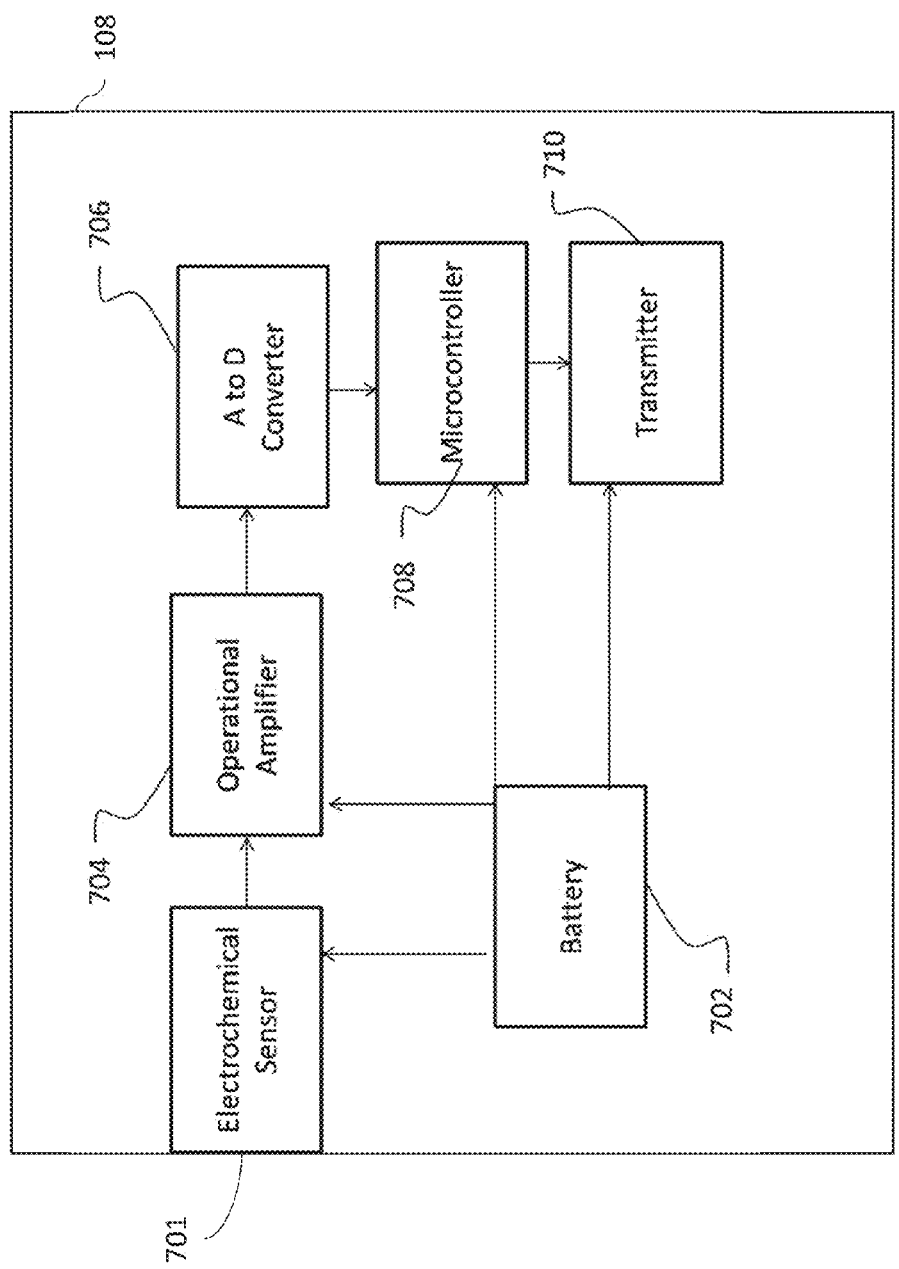
FIG. 7 is a schematic diagram of electrical components in a device body.

Referring to the schematic diagram of FIG. 7, the device body 108 includes an electrochemical sensor 701, a battery 702, an operational amplifier 704 (e.g., LMP91002), an analogue-to-digital converter 706, a microcontroller 708, and a transmitter 710 (e.g., a radio transmitter). In an example, the battery 702 powers the operational amplifier 704 to convert the small currents created from the sensor cartridge 106 via the electrochemical sensor 701 into a voltage. For example, a 1 μA current flowing into the operational amplifier with a feedback resistor of 360 kilo-Ohms, will result in a voltage of 360 mV. This voltage is read by the analogue-to-digital converter 706, and converted into an electrically coded binary sequence that is readable by the microcontroller 708.

The microcontroller 708, also powered by the battery 702, reads a sequence of operations from onboard EEPROM, including operations to send a digital representation of the analogue voltage to a transmitter 710. The transmitter 710 can be a wireless communication unit or circuit such as, for example, a BLUETOOTH LE radio transmitter module.

At step 506 of FIG. 5, a signal based on the electrical current is transmitted to a monitoring device. For example, the transmitter 710, also powered by the battery 702, transmits an electrical signal that includes a digital representation of the analogue voltage to a receiver, such as, for example, a Bluetooth LE receiver. In other examples, the transmitter 710 alternatively or additionally supports near field communication (NFC).

Figure 8:
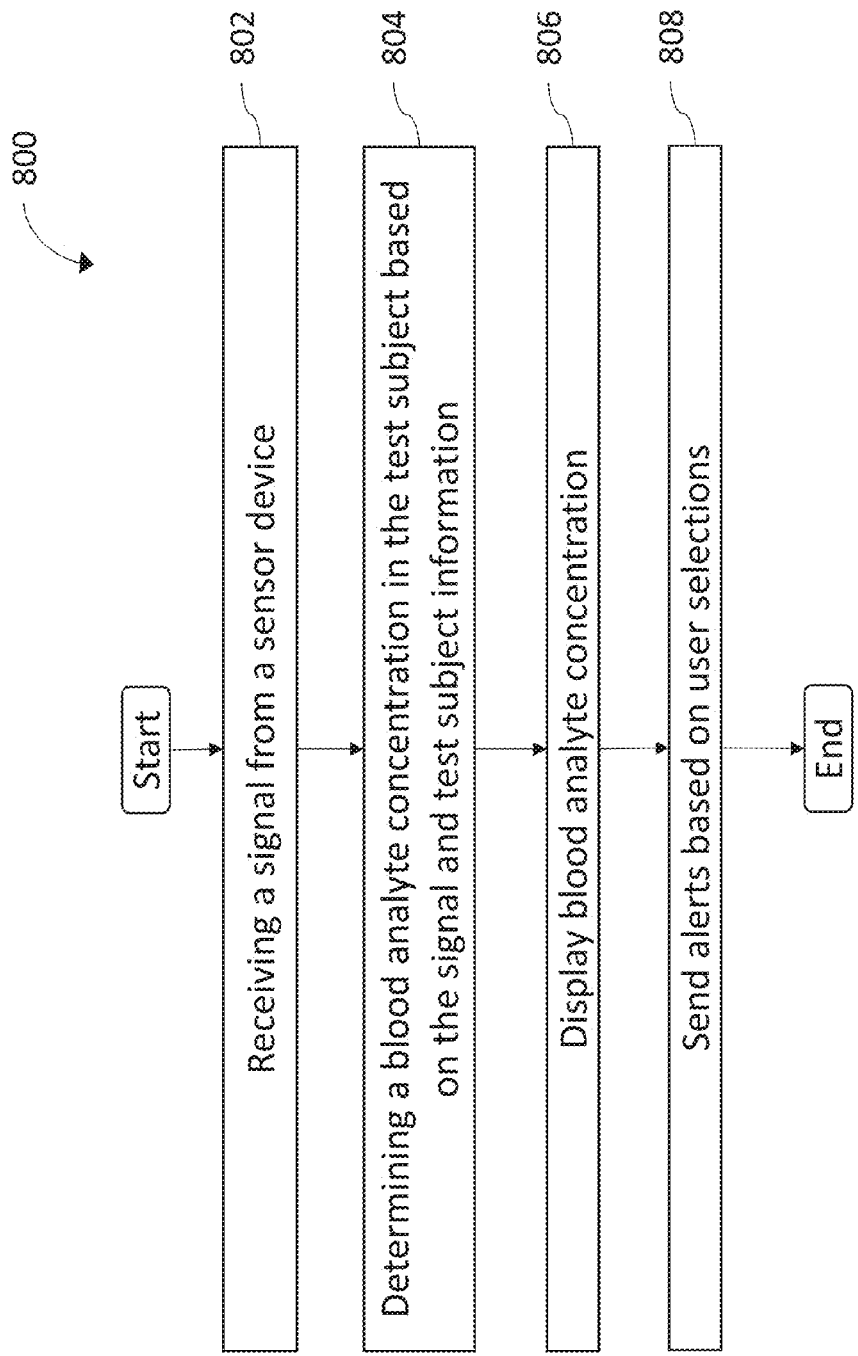
FIG. 8 is a flow chart of a method of determining analyte concentration in a subject.
Figure 9:
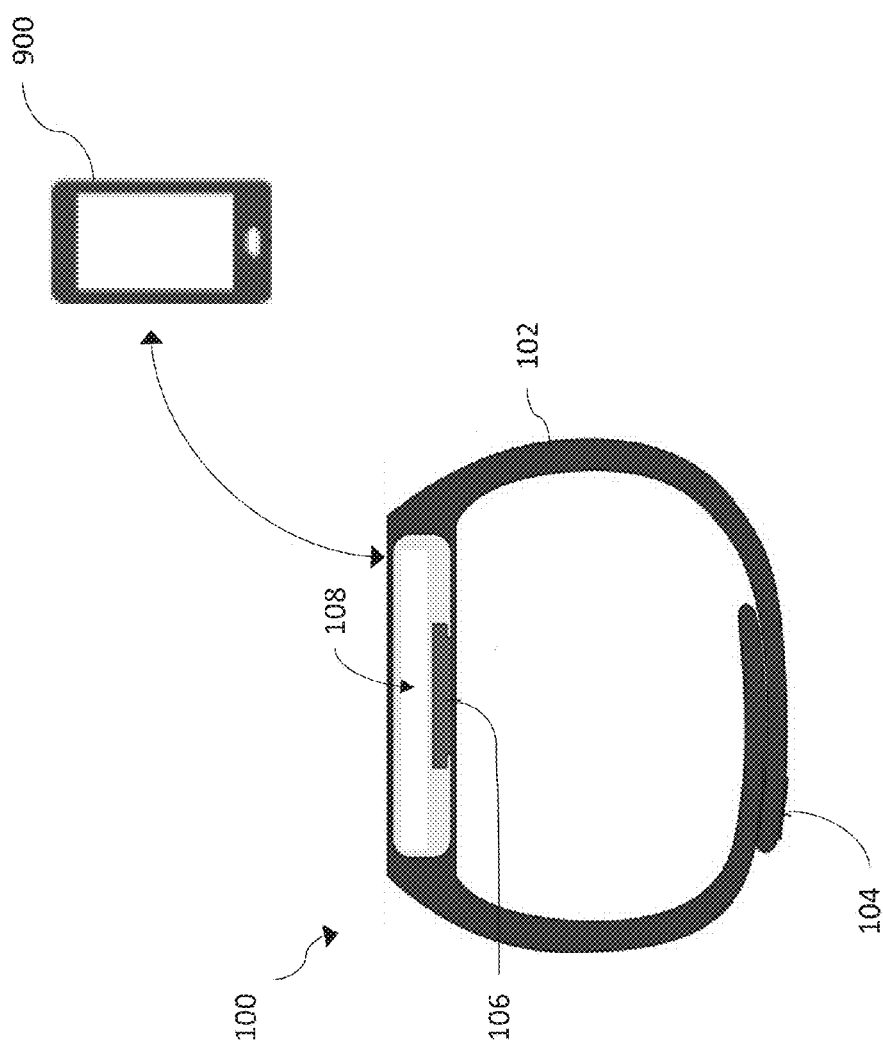
FIG. 9 is a block diagram showing transmission of an analyte concentration signal from a sensor device to a monitoring device.

As shown in the method 800 of FIG. 8, the electrical signal from the sensor device 100 can be used to determine analyte concentration in a subject. In step 802, an application program (or app) on a monitoring device, such as, for example, a smartphone with a Bluetooth LE radio receiver or NFC support, receives the electrical signal from the sensor device 100. FIG. 9 shows the sensor device 100 communicating with a monitoring device 900, such that the application receives the electrical signal from the sensor device 100 and decodes the electrical signal determine a transdermal analyte concentration.

The monitoring device 900 can have a touch screen interface supported by an operating system for receiving user input and displaying information such as graphics and text to the user. The touch screen is used as both an input device and an output device. The monitoring device 900 includes a processor and memory, such as, for example, random access memory (RAM), storage memory, and may include a graphics processor and/or an audio processor. The monitoring device can have multiple hardware features, such as radios, transmitters, transceivers, antennas and electronic chips and firmware that enable the mobile devices to communicate over a data network and a mobile voice network. The hardware features can also include one or more audio speakers to emit sound, and one or more microphones to capture sound. The operating system on the mobile devices provides software support to the application and enables the application to access the hardware features of the mobile devices. The monitoring device 900 can also support voice and data communications according to multiple communications standards.

At step 804, a blood analyte concentration in the subject is determined by the application based on the electrical signal and optionally subject information. The transdermal analyte concentration is converted to an estimate of blood analyte concentration using a deconvolution algorithm. The deconvolution algorithm may use information entered into the application, typically by the target subject, to estimate a blood analyte concentration in the target subject. For example, information entered by the subject can include the target subject's skin type, metabolism, sweat rate, gender, height, weight, physical condition, activity profile, blood pressure, heart rate, and alcoholic beverage consumption. This information can improve precision of the estimated blood analyte concentration by the application.

By using estimates of physical parameters along with a model for metabolism and diffusion through the skin, the lag-time inherent to, for example, transdermal alcohol sensing can be minimized to more closely approximate actual blood alcohol concentration. For example, an individual that is not sweating and whose skin follows a Fickian model for diffusion with known permeability will have a sensor response that is well-defined, effectively a convolution of blood alcohol concentration with a skin transfer response function. With knowledge of the transfer function, the sensor can more accurately estimate blood alcohol concentration by means of deconvolution of the skin transfer function. However, inaccuracies in the model of the transfer function can result in erroneous deconvolution. It is useful to determine user-specific parameters, such as sweat-rate, to provide the most accurate possible model of the skin response function. In the absence of any user-specific information, a mean skin-response function may be used, to give a reasonable average response time.

Lag-time between blood alcohol concentration and transdermal alcohol concentration can be minimized by ensuring that the user is sweating profusely (for example by use of iontophoresis), by maximizing the permeability of the skin (for example with olive-oil or other skin moisturizing creams), or by abrasion of the skin (for example using a pumice-stone skin treatment prior to application of the sensor).

At step 806, the monitoring device displays an estimated blood analyte concentration determined by the application. The subject could then view the estimated blood analyte concentration. In an example where a blood alcohol concentration is determined, the subject could use this information to decide whether to temporarily stop drinking alcohol, or legally drive a vehicle or operate a boat.

At step 808, the monitoring device can provide alerts based on user selections. For example, an alert can be provided to the subject via the monitoring device, when a certain blood analyte concentration level is reached. The alert could be audio, vibration and/or visual. In another example, an alert in the form of a text message or email note can be sent to friends of the subject via the subject's mobile device when a certain blood analyte concentration level is reached. The alert could optionally include a location of the subject. In another example, the application could send the subject targeted advertisements.

Figure 10A:
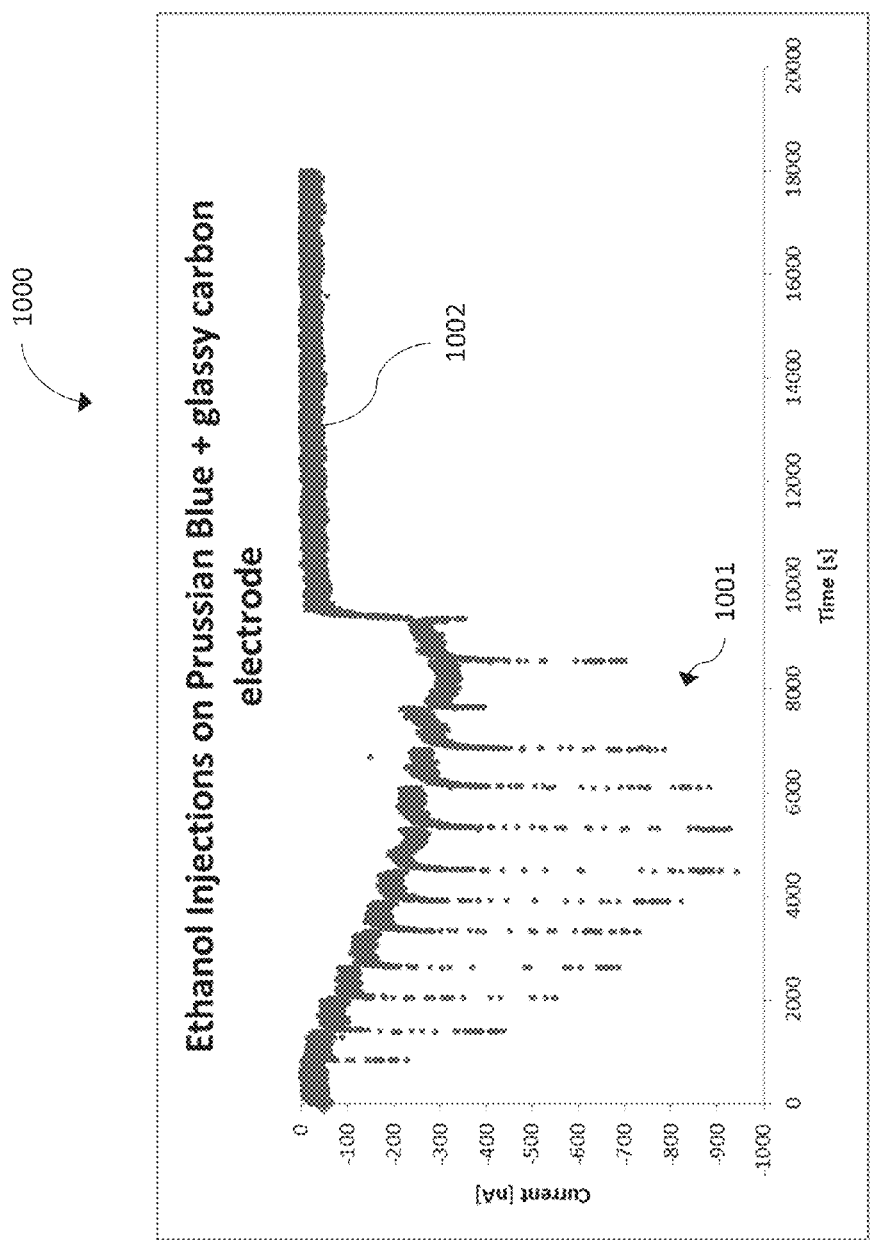
FIG. 10A is a graph of current versus time showing an electrical current in a sensor device in response to temporally spaced in vitro injections of ethanol.

FIG. 10A demonstrates how the sensor device responds to the introduction of ethanol, and shows a graph 1000 of current versus time for electrical current in a sensor device in response to temporally spaced in vitro injections of ethanol. In this example, a working electrode of 1 mm diameter glassy carbon rod with Prussian Blue was measured at 0V potential with respect to a silver chloride counter/reference electrode in a buffer of 1X PBS. Ten injections of ethanol 1001 were added to a solution of alcohol oxidase in increasing increments of 40 µM, up to a total of 400 µM, and the electrical current was measured continuously at increments of one data-point per second. After the injections, the electrode was flushed with PBS, and the signal returned to the baseline value 1002.

Figure 10B:
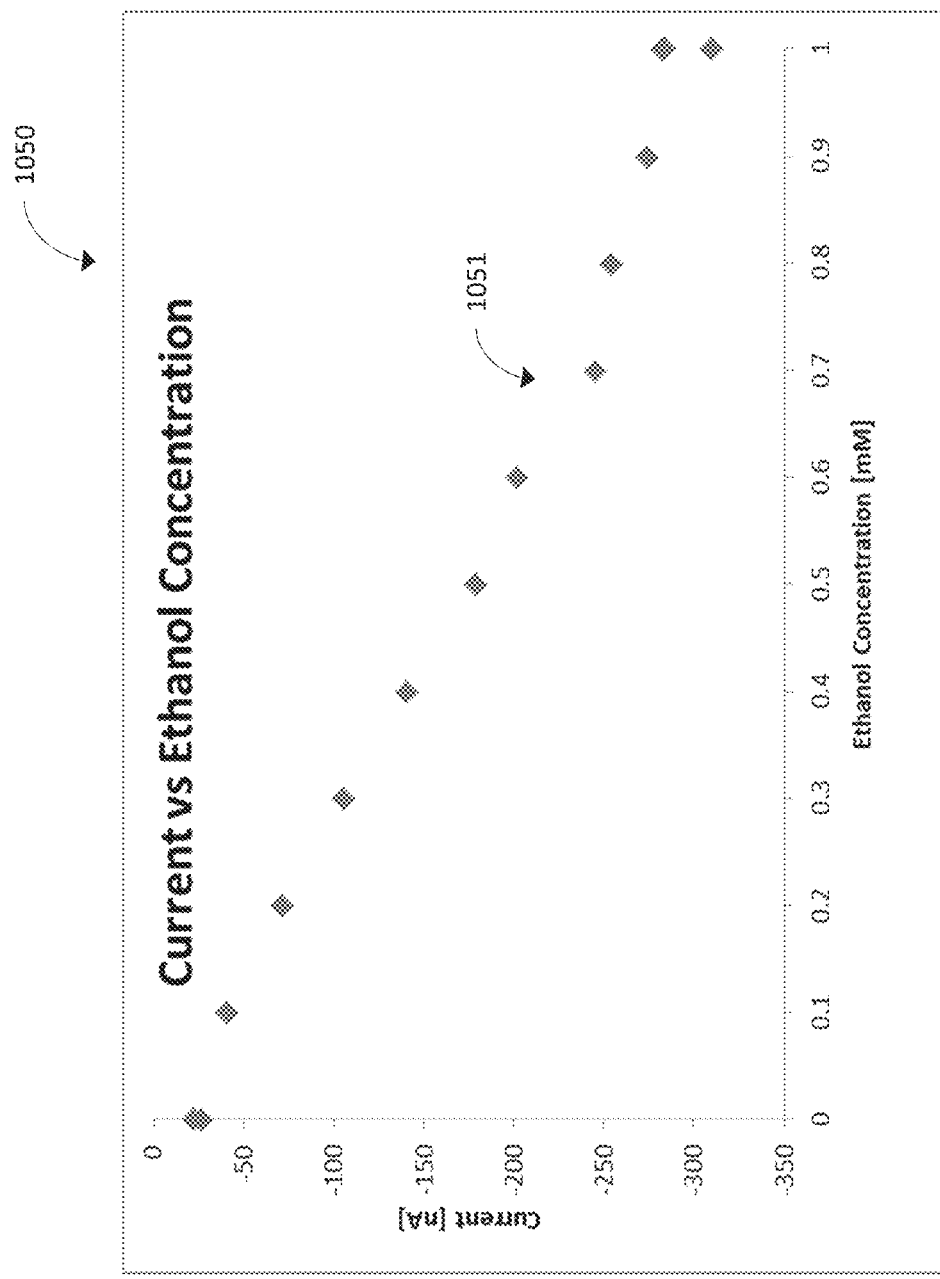
FIG. 10B is a graph of current versus ethanol concentration for the sensor device in response to injections of ethanol.

FIG. 10B shows a graph 1050 of current versus ethanol concentration for the sensor device, where the average steady-state electrical current after injections is shown as a function of total ethanol concentration. The sensor device has an approximately linear response 1051 in the range of 0.2 mM to 0.6 mM, with resulting currents of approximately −100 nA and −250 nA, respectively.

Figure 11:
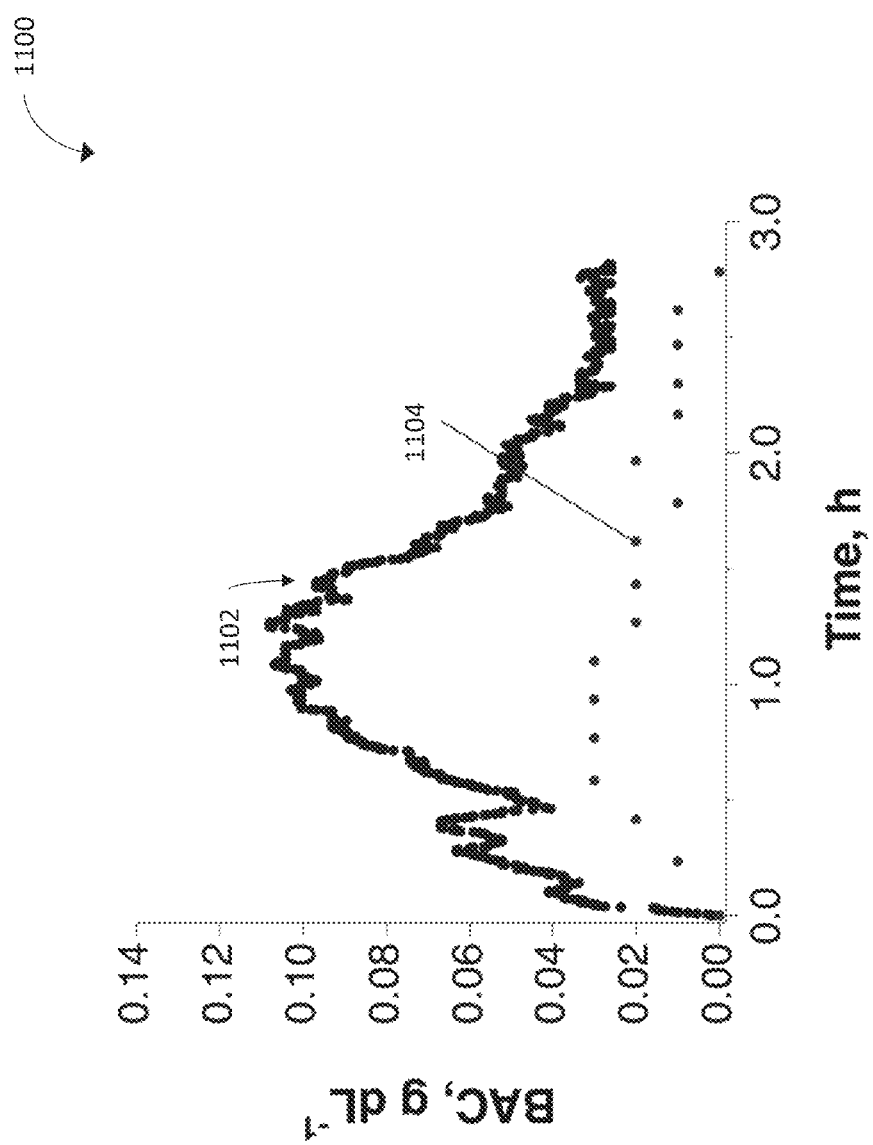
FIG. 11 is a graph of current versus time showing an electrical current in a sensor device worn by a 155-pound male subject in response to consumption of an alcoholic beverage.

FIG. 11 demonstrates how the sensor device responds to consumption of alcoholic beverages by a subject, and shows a graph 1100 of current versus time for electrical current in a sensor device worn by a 155-pound male subject in response to consumption of alcoholic beverage. The sensor device used to generate this data includes a graphite/Teflon electrode with integrated alcohol oxidase, horseradish peroxidase, and ferrocene, in PBS. The sensor device also has a polyethylene membrane of 1.27 cm$^2$ area and a thickness of 17 micrometers, and a 0V applied potential with respect to a silver-chloride electrode. In this example, the subject drank three ounces of a 40% alcoholic beverage in ten minutes, and his blood alcohol content was continuously monitored for three hours with both the sensor device, plot 1102, and a commercial breathalyzer, plot 1104. The data collected with the sensor device was transmitted wirelessly via BLUETOOTH LE and retrieved on an iPhone via an application (e.g., the CySmart Temperature Monitor App). The data was securely stored, and subsequently shared on another device by emailing it from the iPhone to an email address via a wireless internet connection. The measurements carried out with the commercial breathalyzer were recorded every 10 minutes.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the methods described herein. Acts, elements and features discussed only in connection with one embodiment are not intended to be excluded from a similar role in other embodiments.

As used herein, "plurality" means two or more. As used herein, a "set" of items may include one or more of such items. As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, "and/or" means that the listed items are alternatives, but the alternatives also include any combination of the listed items.

It is claimed:

1. A transdermal analyte sensor device comprising:
   a sensor cartridge comprising:
      a membrane permeable to a target analyte transdermally received from a subject,
      a reservoir containing a fluid to receive the target analyte through the membrane and an enzyme to react with the target analyte to form a byproduct,
      a working electrode to generate an electrical current based on a concentration of a byproduct, and
      a cartridge electrical contact disposed on a flange to transmit the electrical current from the working electrode; and
   a device body comprising:
      a device electrical contact to receive the electrical current from the cartridge electrical contact,
      a transmitter to transmit a signal based on the electrical current to a monitoring device, and
      a cartridge receptacle configured to slidably receive the sensor cartridge and position the membrane to contact skin of the subject, wherein when the sensor cartridge is slidably received in the cartridge receptacle, the flange is received in a recess of the cartridge receptacle such that the cartridge electrical contact is electrically coupled to the device electrical contact.

2. The transdermal analyte sensor device of claim 1, wherein the analyte is ethanol.

3. The transdermal analyte sensor device of claim 1, wherein the analyte is urea.

4. The transdermal analyte sensor device of claim 1, wherein the analyte is glucose.

5. The transdermal analyte sensor device of claim 1, wherein the enzyme comprises alcohol oxidase.

6. The transdermal analyte sensor device of claim 1, wherein the enzyme comprises horseradish peroxidase.

7. The transdermal analyte sensor device of claim 1, wherein the working electrode comprises glassy carbon.

8. The transdermal analyte sensor device of claim 7, wherein the working electrode is coated with Prussian Blue.

9. The transdermal analyte sensor device of claim 1, wherein the membrane comprises polyethylene.

10. The transdermal analyte sensor device of claim 1, wherein the membrane comprises nylon.

11. The transdermal analyte sensor device of claim 1, wherein the sensor cartridge further comprises a reservoir electrode to transmit the electrical current.

12. The transdermal analyte sensor device of claim 11, wherein the reservoir electrode comprises silver.

13. The transdermal analyte sensor device of claim 11, wherein the reservoir electrode comprises a silver-chloride coating.

14. The transdermal analyte sensor device of claim 1 further comprising a wristband to fasten the sensor device to the subject.

15. The transdermal analyte sensor device of claim 1, wherein a fluid seal between the membrane and the sensor cartridge maintains the fluid in the reservoir.

16. The transdermal analyte sensor device of claim 1, wherein the analyte passes through the membrane and into the reservoir as a fluid.

17. A method for transdermal analyte sensing using a device having an electrical contact, the method comprising:
transdermally receiving an analyte from a subject through a membrane of a sensor cartridge into a liquid, wherein the sensor cartridge comprises a flange and is configured to be slidably received in a cartridge receptacle of a device body having a device electrical contact to position the membrane to contact skin of a subject;
generating an electrical current based on a concentration of the analyte in the liquid; and
transmitting a signal based on the electrical current,
wherein when the sensor cartridge is slidably received in the cartridge receptacle, the flange is received in a recess of the cartridge receptacle such that the cartridge electrical contact is electrically coupled to the device electrical contact.

18. The method of claim 17, wherein the analyte is ethanol.

19. The method of claim 17, wherein the analyte is glucose.

20. The method of claim 17, wherein the analyte is urea.

21. A method for determining blood concentration of an analyte in a subject, the method comprising:
receiving a signal from a device, the signal based on a concentration of a liquid analyte transdermally received from the subject through a membrane of a sensor cartridge, wherein a cartridge receptacle comprises a flange and is configured to be slidably received in a cartridge receptacle of a device body having a device electrical contact to position the membrane to contact skin of the subject; and
wherein when the sensor cartridge is slidably received in the cartridge receptacle, the flange is received in a recess of the cartridge receptacle such that the cartridge electrical contact is electrically coupled to the device electrical contact, and
displaying a blood analyte concentration based on the signal.

22. The method of claim 21, wherein the analyte is ethanol.

23. The method of claim 21, wherein the analyte is glucose.

24. The method of claim 21, wherein the analyte is urea.

25. The method of claim 21 further comprising:
receiving subject information; and
displaying the blood analyte concentration further based on the subject information.

26. The method of claim 21 further comprising:
receiving alert criteria; and
sending an alert based on the alert criteria and the blood analyte concentration.

* * * * *